(12) United States Patent
Volker

(10) Patent No.: US 10,307,715 B2
(45) Date of Patent: Jun. 4, 2019

(54) CONTROL OF AN RO INSTALLATION FOR FLUSHING SOLUTIONS

(71) Applicant: Manfred Volker, Blankenbach (DE)

(72) Inventor: Manfred Volker, Blankenbach (DE)

( * ) Notice: Subject to any disclaimer, the term of this patent is extended or adjusted under 35 U.S.C. 154(b) by 56 days.

(21) Appl. No.: 14/950,271

(22) Filed: Nov. 24, 2015

(65) Prior Publication Data

US 2017/0021308 A1 Jan. 26, 2017

(30) Foreign Application Priority Data

Nov. 25, 2014 (DE) .................. 10 2014 017 404

(51) Int. Cl.

| | |
|---|---|
| *B01D 65/10* | (2006.01) |
| *B01D 61/12* | (2006.01) |
| *B01D 61/08* | (2006.01) |
| *B01D 61/02* | (2006.01) |
| *C02F 1/44* | (2006.01) |
| *G01N 15/08* | (2006.01) |
| *G01N 27/08* | (2006.01) |

(Continued)

(52) U.S. Cl.
CPC .............. *B01D 65/10* (2013.01); *B01D 61/02* (2013.01); *B01D 61/025* (2013.01); *B01D 61/08* (2013.01); *B01D 61/12* (2013.01); *C02F 1/441* (2013.01); *G01N 15/08* (2013.01); *G01N 27/08* (2013.01); *G01N 27/12* (2013.01); *B01D 2311/243* (2013.01); *B01D 2311/25* (2013.01); *C02F 1/444* (2013.01); *C02F 2103/026* (2013.01); *C02F 2103/04* (2013.01); *C02F 2209/02* (2013.01); *C02F 2209/03* (2013.01); *C02F 2209/05* (2013.01); *C02F 2209/40* (2013.01); *C02F 2209/42* (2013.01); *G01N 2015/086* (2013.01)

(58) Field of Classification Search
CPC .......... B01D 2311/243; B01D 2311/25; B01D 61/02; B01D 61/025; B01D 61/08; B01D 61/12; B01D 65/10; C02F 1/441; C02F 1/444; C02F 2103/026; C02F 2103/04; C02F 2209/02; C02F 2209/03; C02F 2209/05; C02F 2209/40; C02F 2209/42; G01N 15/08; G01N 15/086; G01N 27/08; G01N 27/12

See application file for complete search history.

(56) References Cited

U.S. PATENT DOCUMENTS

| | | | |
|---|---|---|---|
| 6,096,007 A | 8/2000 | Haan et al. | |
| 6,280,632 B1 * | 8/2001 | Polaschegg | ......... A61M 1/3462 210/103 |

(Continued)

FOREIGN PATENT DOCUMENTS

| | | |
|---|---|---|
| DE | 1955538 | 12/1966 |
| DE | 3315031 A1 | 1/1985 |

(Continued)

*Primary Examiner* — John Kim
(74) *Attorney, Agent, or Firm* — Greer, Burns & Crain, Ltd.

(57) ABSTRACT

The method of verifying an RO membrane of an RO installation is characterized in that the conductivity values of the supplied raw water and of the permeate and the amount of the raw water inflow and the concentrate outflow are continuously or cyclically measured and that the efficiency of the RO membrane, its retention rate and/or filtration efficiency are calculated from the measured values.

3 Claims, 6 Drawing Sheets

(51) Int. Cl.
*G01N 27/12* (2006.01)
*C02F 103/02* (2006.01)
*C02F 103/04* (2006.01)

(56) References Cited

U.S. PATENT DOCUMENTS

| | | |
|---|---|---|
| 7,635,359 B2 | 12/2009 | Nakazawa et al. |
| 2003/0230533 A1* | 12/2003 | Gross ................ A61M 1/16 210/646 |
| 2005/0171501 A1* | 8/2005 | Kelly ............... A61M 1/3462 604/500 |
| 2011/0042202 A1 | 2/2011 | Pettee et al. |
| 2011/0284464 A1* | 11/2011 | Roncadi ............ A61M 1/16 210/647 |
| 2012/0298569 A1* | 11/2012 | Volker ............. B01D 61/025 210/198.1 |

FOREIGN PATENT DOCUMENTS

| | | |
|---|---|---|
| DE | 4121568 A1 | 10/1992 |
| DE | 4122171 A1 | 1/1993 |
| DE | 4137748 A1 | 5/1993 |
| DE | 4332070 A1 | 3/1995 |
| DE | 69318988 T2 | 3/1996 |
| DE | 19538818 | 4/1997 |
| DE | 19733278 A1 | 2/1999 |
| DE | 102009057562 A1 | 6/2011 |
| DE | 102010055781 A1 | 6/2012 |
| DE | 102011102662 A1 | 11/2012 |
| DE | 102012001879 A1 | 8/2013 |
| EP | 2689790 | 7/2012 |
| EP | 2674399 | 12/2013 |
| WO | 2005077335 A1 | 8/2005 |

* cited by examiner

CONTROL OF AN RO INSTALLATION FOR FLUSHING SOLUTIONS

FIELD OF THE INVENTION

The subject application relates to medical flushing solutions, and more particularly to a control of a reverse osmosis (RO) installation for flushing solutions.

SUMMARY OF THE INVENTION

The object of this development is to produce an economical, chemically and microbiologically ultrapure liquid decentrally in situ as a base material for the use of medicinal flushing solutions from (pre-treated) tap water by the use of filter technology in order to achieve economic and application-technical advantages.

A verifiable liquid quality is to be achieved and the expense necessary for the purification steps and toxic substances is to be limited. An environmentally friendly technology and an intelligent evaluation of the data are to improve the service life of the components used or detect their wear in a timely manner.

Use of this development for other fields, such as liquid preparation for the laboratory, for biology and pharmacy as an ultrapure flushing agent or also as an additive medium for the production of medicines, cell cultures and the like is conceivable and practicable.

Medicinal flushing solutions are generally further processed from distilled water as the base material, which is produced centrally, in a central production process to make flushing solutions.

The regulative and normative requirements as regards the quality of the base material, namely water, are so high that it was previously not possible to produce verifiable flushing solutions, when required, in situ, e.g. in a hospital.

These are, on the one hand, the high microbiological requirements and, on the other hand, the necessary chemical requirements as regards the base material, namely water, which conflict with a verifiable and detectable, normatively required quality of the production in situ in accordance with requirements.

Laboratory water devices are available on the basis of reverse osmosis for producing liquid with a high chemical and microbiological purity but the lacking prevention for germ reduction and a non-verifiable test of the filter stages involved are considered to be disadvantageous.

A further significant requirement with the online production of a flushing solution is the necessary high availability of the devices.

A problem which is difficult to solve is to permanently minimise or preventatively to reduce the rapid microbiological colonisation within the filter stages or the water treatment. Minimisation and prevention are necessary because the filter stages exhibit only a limited germ retention by the primary and secondary sides. Water samples must therefore consequently frequently be removed and expensive microbiological tests performed as a quasi revalidation.

The filter stage used for the retention of the chemical components, preferably in the form of a reverse osmosis membrane, may also be diagnosed only with difficulty as regards potential extremely small ruptures. A conductivity measurement as the only verification of an osmosis membrane—as is used in the prior art—is not sufficient.

Germ reduction in water-conducting systems is conventionally performed physically and/or chemically. Large expense is incurred by reason of the toxicity, and the detection control after chemical disinfection because the smallest residual concentrations can result in serious harm to patients. Furthermore, the waste water is contaminated by the use of chemicals or biocides.

Thermal disinfection is frequently not sufficient to completely reduce germs and material stress and the premature ageing of the components used can also not be ignored. The basic disadvantage of thermal disinfection is, however, the low purification effect, e.g. of the primary side of a reverse osmosis membrane. It has transpired that, depending on the nature of the contamination present, compression or crustification of a coating that is present can be the result of thermal disinfection.

A combination of thermal and chemical should ideally be selected in order to achieve both a cleaning and also a disinfecting action. By reason of the resultant high effectiveness, a lower temperature would be necessary and the concentration of the chemical agent could be lower. Practice, however, reveals considerable difficulties as regards the transmembrane flow of a chemico-thermal cleaning solution from the primary to the secondary side of the reverse osmosis membrane because the high osmotic pressure opposes the transmembrane pressure.

The basis for perfect water quality is also high availability and also a reliable, controllable, chemical and microbiological retention rate of the filter stages involved. In the prior art, e.g. with reverse osmosis membranes, a conductivity measurement is performed, the informative value of which as regards the membrane quality can be criticised as inadequate.

Due to the aforementioned difficulties, filters with low service lives are therefore commonly used in practice which need to be replaced after being used for a short period of time.

The object of the invention are necessary improvements and therefore economical online production of ultrapure water for medicinal flushing solutions based on reverse osmosis with extremely low, normatively acceptable microbiological and chemical contamination without further checks at the place of use.

The necessary high availability of the devices should exhibit only a remote probability of failure in all measuring and control tasks as regards their intrinsic reliability in order to prevent catastrophic consequences for the patients under all circumstances or to perfectly control the quality or also the toxicity of the liquid produced within the guaranteed acceptance criteria.

This object is effectively solved in accordance with the invention in that to produce the ultrapure water the combination of a reverse osmosis membrane and at least one further, subsequent filter stage, for instance an Ultrafilter or sterifilter, preferably in the form of a capillary membrane is used.

The cleaning of the system or germ prevention and reduction is effected by the combination of a citrate-based disinfection and cleaning agent of low toxicity with a heating of the water. The primary and also the secondary side of the reverse osmosis are thereby to be disinfected or cleaned separately from one another by means of an additional pump, also without transmembrane flow.

The supply of the disinfectant solution and cleaning solution occurs highly advantageously without the assistance of the user to the secondary side of the membrane and can be distributed from there, as required, into the primary circuit also.

In order that an undesired, unintended supply of disinfecting/cleaning agent is prevented, the disinfection device includes a level-controlled glass chamber with forced ventilation in the inlet system which permits reliable media separation and is usable at the same time as an empty indicator for the disinfecting/cleaning agent supply.

In order to avoid dead zones and residues of cleaning agent, the membrane is inserted free of dead zones into the reverse osmosis module and the feed tank is thoroughly flushed in an annular manner at its inner wall surface.

Checking and securing the disinfecting agent freedom is effected by two mutually verifying conductivity measurements, by whose approval signal a permeate release valve can be switched.

The verification of the reverse osmosis membrane is effected with advantage substantially by a continuous measurement and a trend analysis of the retention rate and yield, i.e. the ratios of the conductivity values of the primary to the secondary side of the membrane and the ratio of the raw water used to the permeate volume. A standardised permeate flow is also determined.

The trend of the detected data with adjustable boundary values can thereby be controlled and displayed by means of different independent computers.

Prognoses relating to service operations or other quality and service life maintaining features can advantageously be derived from this information.

If a discrepancy occurs, an information, warning or alarm signal can also be generated and output, which gives the operator an indication of the worsening membrane quality.

For the purpose of a better overview, all process data for separating data determination and control are shown in the following table.

Maintenance of normative requirements is thus possible, as also is the control of the performance parameters of the osmosis membrane.

Altogether, the process data shown below are collected.

| Process data |
|---|
| Maximum raw water inflow |
| Permeate consumption |
| Raw water consumption |
| Inflow temperature |
| Permeate temperature |
| Raw water conductivity |
| Permeate conductivity |
| Yield |
| Retention rate |
| Standard permeate flow |
| Pressure holding test Ultrafilter/sterifilter F1 |
| Pressure holding test Ultrafilter/sterifilter F2 |
| Disinfection detection |
| Chlorine content in the raw water |
| Water hardness |
| Optionally permeate and/or concentrate pressure |

Electronics and software are implemented as an operating and protective computer system, the signals from which communicate and compare safety-relevant data with one another and thus prevent breakdown with the potential for danger.

All process-relevant data both from the operating computer and also from the protective computer are in principle gathered and optionally evaluated. The measurement results are sent from the operating computer to the protective computer and vice versa. Each computer compares the measurement results with its own and sends back a confirmation.

After the confirmation from the operating and safety computers, the data is written together with a check total into the trend data store, which can preferably be instructed in the form of an Eprom or also as another storage medium.

Specifically, the following data are important for the assessment and verification of the reverse osmosis membrane:

Monitoring of the Efficiency (Yield):

The efficiency of the reverse osmosis membrane is calculated from the ratio of the volume of the permeate to the volume of the supplied raw water.

$$\eta = \frac{Q_{raw\ water} - Q_{concentrate}}{Q_{raw\ water}}$$

$\eta$=efficiency in %
$Q_{raw\ water}$=amount of the raw water in L/min
$Q_{concentrate}$=amount of the water which contains the chemical constituents in an increased concentration.

As a result of the monitoring of the efficiency, control, in particular, of the concentration of the low-solubility salts, such as potassium and magnesium salts on the primary side of the membrane, is possible. An increased efficiency indicates that less chemical constituents can be retained and/or a blockage of the membranes can occur.

For the purpose of precise determination, two flow meters (FM-raw water and FM-concentrate) are necessary, whereby one of these (FM-RW) is regularly volumetrically verified and thereafter the relative agreement of the two flow meters is checked and monitored by different computers.

In order that an exact volumetric check of the FM-raw water is possible, the liquids are fed into the feed tank with a calm flow via an annular gap.

Monitoring of the Retention Rate:

The average retention rate can, for instance, be calculated from the ratio of the permeate conductivity to the supplied conductivity of, for instance, the raw water or very generally the determined conductivity of the liquid on the primary side of the membrane.

$$R = 1 - \frac{2 * C_{permeate}}{C_{raw\ water} * \left(\frac{1}{1-\eta} + 1\right)}$$

R=current retention rate in %
$C_{permeate}$=conductivity of the permeate in uS/cm
$C_{raw\ water}$=conductivity of the raw water in uS/cm
$\eta$=efficiency (yield) in %
• Unit: dimensionless or %

The filtration efficiency and the concentrate on the primary side of the reverse osmosis membrane which is used can be assessed by means of the retention rate. The effective conductivity of the raw water and of the permeate are thus measured cyclically and the current retention rate is calculated therefrom. The mean value of the retention rates is calculated from n=values and stored. A retention trend is continuously observed. In the event of a decline in the retention rate, for instance of more than 10%, a procedure can be recommended and/or be automatically initiated. For instance, cleaning of the membrane, if necessary replacement of the membrane and/or chemical analysis of the permeate.

Permeate Conductivity:

The measurement results of the permeate conductivity are required to determine the retention rate. In, practice, this measured value is used as the only quality feature to assess the reverse osmosis membrane.

In order to make a determination in a first error-safe manner, three conductivity measurement devices can be used. Firstly, a conductivity meter in the raw water region or primary region of the membranes and two further meters in the permeate region, whereby the two conductivity measurement devices located in the permeate region are verified by different computers to a high relative conformity of more than 90% and the third conductivity measuring device in the raw water region is also checked for relative correspondence on the basis of the previously determined permeate conductivity and the yield with a calculated expected value.

Since the conductivity of natural water is temperature dependent, the indicated value is compensated with a factor of ca. 2%/° C.

Standard Permeate Flow:

For a supplementary verification of the membrane integrity, a standard permeate flow monitor is provided. The permeate output measured during a test cycle is in each case related to 15° C. and a fixed transmembrane pressure.

As a result of the monitoring of the standard permeate flow, the trend of the transmembrane flow can advantageously be observed for a longer period of time. The occurrence of deposits (fouling) on the reverse osmosis membrane or other factors which lead to impairment or changes in the filtration performance may be indicated.

As a result of the trend assessment, cleaning or other steps are predictable, if the standard permeate flow has decreased, for instance by 10 to 15%.

$$Q_{pStd} = (Q_{rw} - Q_c) * (1 + (T_p - 15) * 0.02)$$

$Q_{pStd}$=standard permeate flow
$Q_{rw}$=raw water flow
$Q_c$=concentrate flow
$T_p$=permeate temperature
0.02=compensation factor (2%/° C.)

Implementation: The difference between the current raw water flow and concentrate flow is initially produced, i.e. the permeate volume is measured and the standard permeate flow at 15° C. is calculated therefrom.

Since the filtration output of the membrane is temperature dependent, an appropriate factor of 2%/° C. is introduced.

For the purpose of exact determination, two flow meters (FM-raw water and FM-concentrate) are necessary, whereby one of these, the raw water inflow meter (FL-RW) is regularly volumetrically verified. Furthermore, the relative agreement of the two flow meters is checked and monitored by different computers.

For the purpose of display, for instance all values are determined and recorded for a period of time which may be selectively determined, e.g. of 50 operating hours, this can correspond to the average operating time per week of an RO installation.

For the purpose of the recording itself, a running average is formed in accordance with the following formula: X $$\overline{X}_{n+1} = \frac{n\overline{X}_n + X_{n+1}}{n+1}$$

where
$\overline{X}_{n+1}$=rolling average value over "n+1" values
$\overline{X}_n$=rolling average value over "n" values
$X_{n+1}$=current measured value
n=number of the values already taken into account For the determination of values between 2 measured values, a time period, for instance, of x seconds or only once per day is used.

Filter and Protection System

In order to ensure the microbiological quality of the permeate, there is advantageously an Ultrafilter or a Sterifilter on the primary side in the permeate circuit. A further Sterifilter can be used to improve the liquid purity downstream, directly at the extraction point. Liquid can with advantage flow over the primary sides of the filters and be cleaned.

Ensuring the filter integrity can be effected by a Bubble Point test. The Bubble Point test is based on the fact that the liquid is retained in the pores of the filter by the surface tension and capillary forces. The minimum pressure which is necessary in order to force liquid out of the pores is a measure of the pore diameter, $$\Delta P = \frac{4 * \sigma * \cos\theta}{D}$$

$\Delta P$=pressure difference in bar
$\sigma$=surface tension of the liquid in N/m (water=72.75 mN/m)
$\theta$=contact angle between liquid and polyethersulfone: 65-70°
D=pore diameter in µm Implementation: The pressure on the filter is increased. At the moment at which a continuous discharge of air bubbles is to be seen the pressure is read off from the manometer. Since the surface tension, angle of wetting and pressure difference are known, a maximum permissible diameter of the membrane pores can be calculated by rearrangement of the equation and thus a conclusion drawn about quality.

A further preferred possibility resides in the conduct of a pressure holding test.

A leak in the filter or the membrane may be reliably detected by the automated pressure holding test. In this test, a leak in the filter is monitored by way of a pressure drop by means of a pressure sensor. This pressure drop is caused by transmembrane gas diffusion through the filter membrane. The pressure holding value is dependent on the membrane surface, i.e. from the filter volume, the gas diffusion flow through the membrane and on the test pressure.

$$\Delta P = \frac{D * t * Pa}{V}$$

$\Delta P$=pressure difference in bar
D=gas diffusion rate in ml/min
t=time in min.
Pa=atmospheric pressure (1.013 bar)
V=filter housing volume in ml In order to carry out the test, the filter membrane should be completely moist or the filter filled with liquid. For the pressure holding test, the filter is slowly acted upon on one side with a pressure and the liquid displaced. The basis of the pressure holding is that as a result of the hydrophilic membrane, when the membrane is intact no significant transmembrane air transport occurs. The pressure holding can be observed, for instance, for ca. 3 minutes. The pressure drop should not exceed a predetermined limit within this time. For the purpose of an exact determination, a pressure sensor is necessary whose zero point and gradient are regularly verified and checked by different computers.

A blocking valve is advantageously inserted at the filtrate outlet of the filter which stops the permeate flow to the place of use in the event of deviation from predetermined trend data or in the event of defective process data, such as defective conductivity and/or temperature. For the information of the user, corresponding indicator information and acoustic and also optical alarms can be triggered.

DETAILED DESCRIPTION OF PREFERRED EMBODIMENTS

Figure 1:
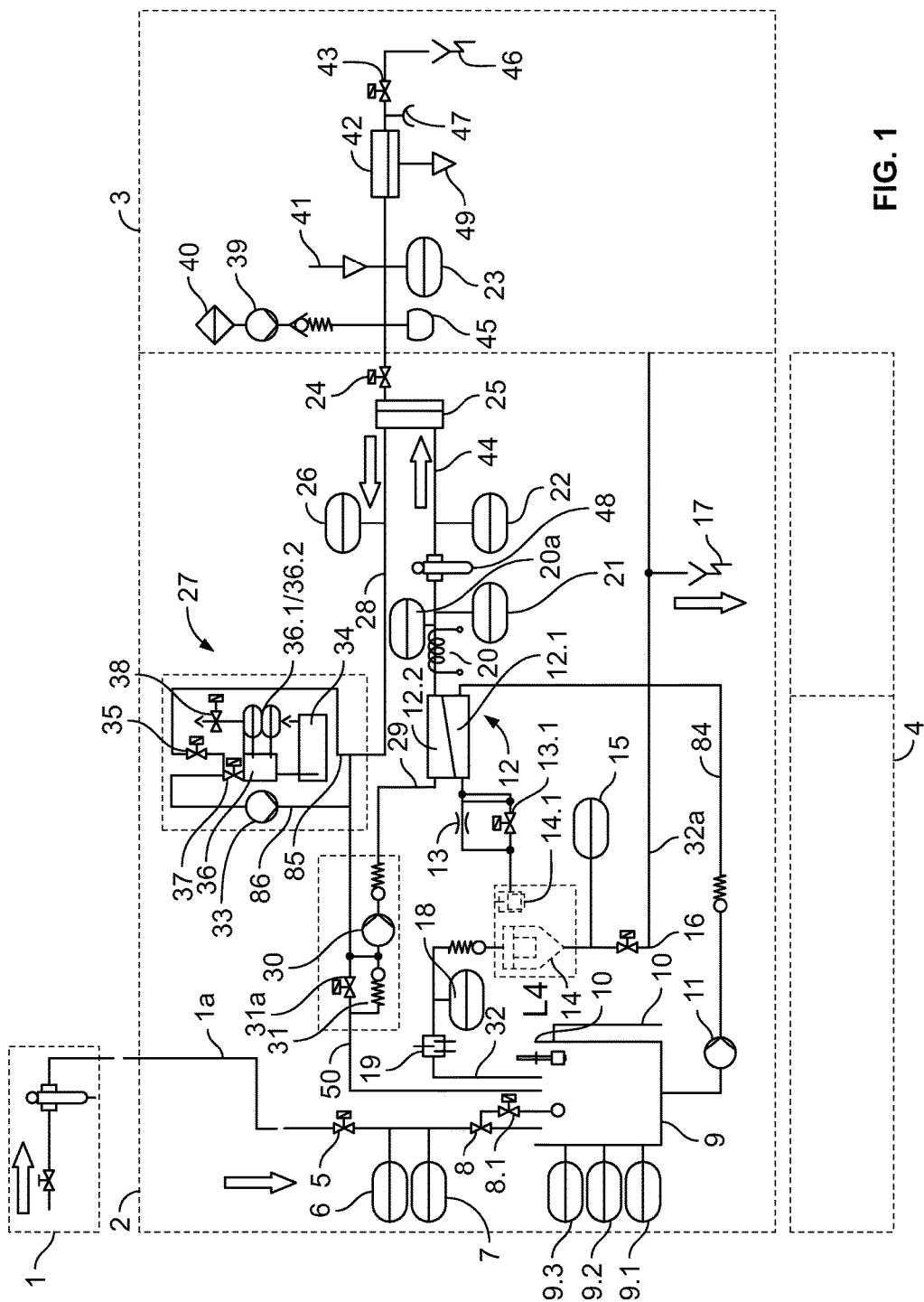
FIG. 1 is a schematic view a RO installation for flushing solutions.

FIG. 1 is a view showing the underlying principle.
Further exemplary embodiments and an indication of possible variants and extensions are shown in FIG. 1 at the same time. Detailed information is given in more detail in the subsequent figures.

The liquid is conducted via an optional pre-filter (1) to the RO installation (2). In the inlet region of the RO installation there is a water inlet valve (5), an inflow flow meter (7) and an inlet conductivity meter (6). The supplied liquid flows via a float-controlled inlet valve (8) via the feed container (9), which is equipped with filling level sensors for determining when it is empty and for filling level control (9.1, 9.2, 9.3).

The float-controlled inlet valve is constructed in the form of a membrane servo valve, the servo bore of which can be closed by extremely low buoyancy forces, that is to say very small float volumes, and thus controls the filling level. There is furthermore the possibility of interrupting the servo flow by means of an electromagnetic valve 8.1 in order thus to prevent the inflow. The liquid can thus reach the feed tank (9) without significant power loss.

The feed tank includes an overflow with a detector (10).
The pump (11) conveys the liquid to the RO membrane (12), whereby the retentate is conveyed on via the flow throttle (13) with high pressure bypass valve (13.1) to the concentrate circulation conduit (32).

In order to maintain a relatively high overflow on the primary side (12.1), the retentate is conveyed back into the feed tank (9). In, order to adjust the efficiency, the outlet flow meter (15) is provided, which, together with the inflow flow meter (7) determines the efficiency calculation by means of the derivation set forth above.

Excess retentate volume or the retentate volume determined from the result of the efficiency calculation is conducted via outlet valve (16) to the discharge (17) and is discarded.

In order to reduce the particles and germs in the retentate flow and for the purpose of decontamination, an optional centrifugal chamber (14) with a cleaning chamber (14.1) is provided. The particles in the retentate are conducted by the centrifugal force to the base of the hopper, collected there and flushed to the discharge (17) with the outlet valve (16) open. In order to improve the flushing process, the high pressure bypass valve (13.1) can be briefly opened in order to achieve a surge-like flushing process.

Decontamination or an influence on the low solubility calcium and magnesium salts can be so effected by means of a cleaning chamber (19)—of the same construction as the cleaning chamber 14.1—, which acts on the liquid by means of voltage pulses or magnetic field effects, that deposition of the same on the primary side (12.1) of the membrane is substantially prevented.

The permeate which is produced is registered by the permeate conductivity monitor (22). Alternatively, a second redundant conductivity measuring cell (23) can also be used.

The permeate released by the conductivity measuring cell (22) is conducted through the Ultrafilter/Sterifilter (25) and the permeate release valve (24) to the filtrate outlet (49).

The permeate flow occurs via conduit (28) either via pressure holding valve (31) and feed tank (9) or by means of permeate circulation pump (30) via conduit (29, 44) in a circuit. As a result of the permeate circulation, liquid flows completely over the primary side of the filter (25) and it is freed of particle residues.

In order to produce a permeate pressure, a pressure holding valve (31) with bypass valve (31a) is used. Excess permeate flows via conduit (50) back to the feed tank (9).

A chemico-thermal disinfection begins with the pump (33) sucking in citrate-containing concentrate from cleaning agent canister (34). The valve (37) is open and flushing valve (35) and forced aeration valve (38) are open. Aeration valve (38) is open with the power off and can be constructed in the form of a spring-loaded hose clamping valve or a lifting valve. The filling level sensors (36.1 and 36.2) attached to the glass protective chamber (36) monitor the suction process and thus also the filling level in the cleaning agent canister (34).

When the pump (30) is running, the disinfecting/cleaning agent is circulated until a predetermined conductivity is achieved. The conductivity concentration can be monitored by means of the measuring device (22). It will be understood that in order to receive the additional liquid valves to the outlet (43) or to the feed tank (31a) are to be briefly opened. The liquid is heated to the desired and pre-set temperature by means of heater (20) and control sensor (21). A chemico-thermal disinfection of the entire ultraclean secondary region (44, 28, 29) up to the permeate outlet (46) is thus selectively possible. The reverse osmosis membrane is wholly cleaned and disinfected via the connections (29, 44) in the ultraclean region.

If required, heated liquid can be conducted to the primary circuit via the opened bypass valve (31a) in order to reach the necessary temperature. As soon as cleaning solution is conducted by means of disinfection device (27) via feed tank (9) into the primary circuit (12.1) of the membrane, the transmembrane flow is interrupted. Pump (11) circulates the primary circuit (84, 12.1, 32, 9) and cleans or disinfects all of the liquid-conducting components in this circuit. After termination of the chemical-thermal disinfection, a flushing clear process can be initiated until conductivity cell (22) and (23) are indicated as being free of disinfecting agent.

During the flushing free process, flushing valve (35) is open in order also to flush free the entire disinfectant-containing conduit of the disinfecting unit (27).

In order to prevent a subsequent, unintended supply of disinfecting agent into the permeate circuit (28), aeration valve (38) is opened and the level in the chamber (36) is monitored. Reliable prevention of an unintended disinfection is thus ensured.

In order to monitor the integrity of the filter (25) or (42) or its membrane, the liquid is forced on the secondary side to the filter (25) and on the primary side to the filter (42) by means of air pump (39) with an optional air suction filter (40). Pressure holding is thus achieved, determined by the hydrophilic character of the membrane, and monitored or registered by means of pressure sensor (45).

(4) indicates only indicatively and by way of example the electronic system, which is constructed in the form of an operating and protective system. A possible addition is also shown in FIG. 1 to the effect that, for instance, a concentrate of a completely ready-for-use flushing solution produced in situ is added in a metered manner by metering device (41), whereby this flushing solution could additionally be filtered in a sterile manner before use by means of filter (42).

Figure 2:
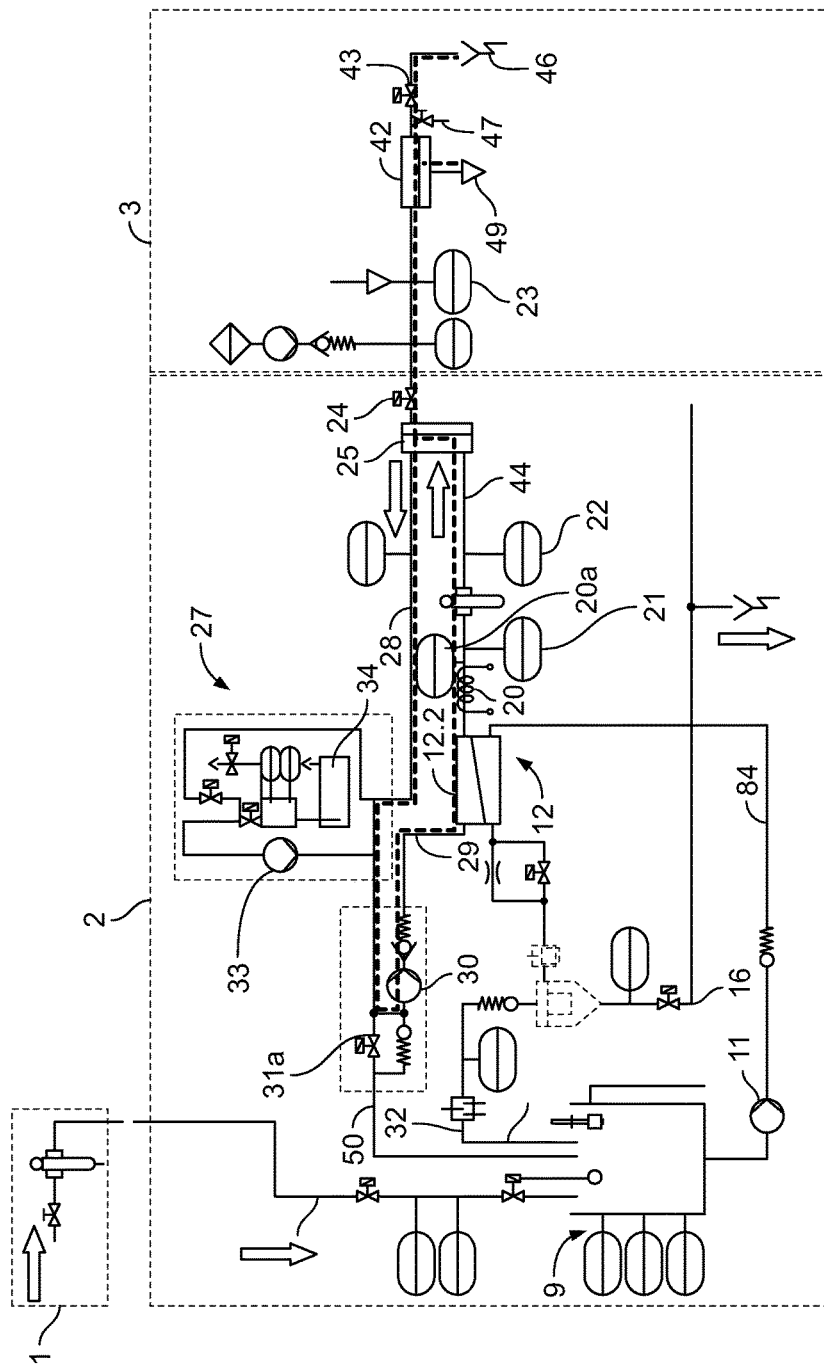
FIG. 2 is a secondary circuit cleaning schematic.
Figure 3:
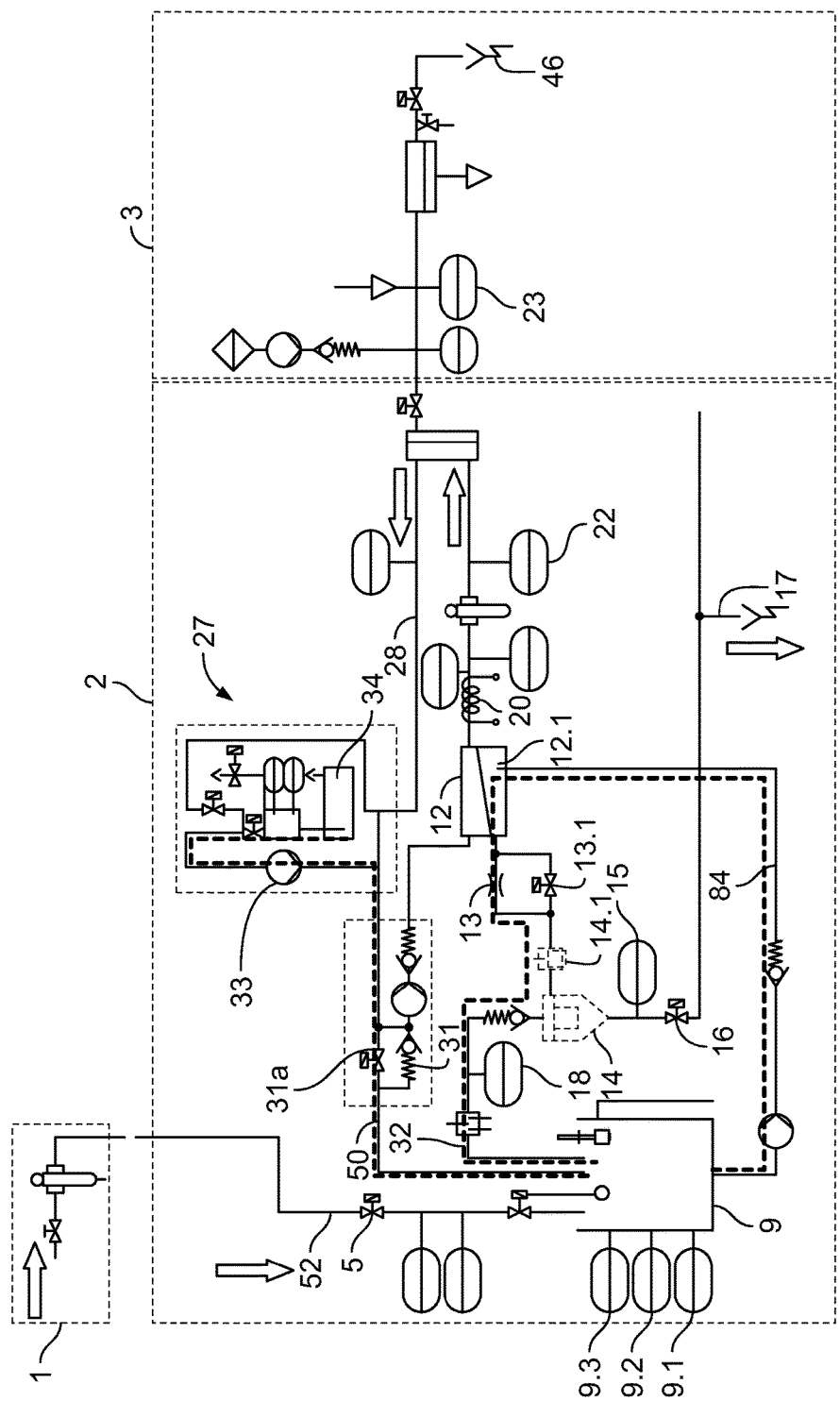
FIG. 3 is a primary circuit cleaning schematic.

In order to explain the cleaning processes, FIGS. 2 and 3 are attached.

FIG. 2 shows the cleaning process of the ultrapure region (44, 28, 29, 12.2) by means of the chain line. The high pressure pump can advantageously be switched on during this cleaning process. The circuit is filled with cleaning agent until a predefined conductivity is reached by means of the disinfecting and cleaning unit (27). During the increase in concentration, valves (24, 43) can briefly be opened.

The permeate circulation pump (30) overflows the circuit so that at the same time disinfecting agent liquid is heated to a predefined temperature by means of heater (20).

The heated disinfecting agent liquid can be bled off to the permeate outlet (46) via the optional sterifilter (42) in order to disinfect this section also.

FIG. 3 shows the hot disinfection of the primary circuit (84, 12.1, 32). Permeate heated by means of heater (20) is firstly conducted into the primary circuit (84, 12.1, 32). During this cycle, the cold liquid can be conducted via valves 16 to the outlet. Disinfecting agent is then conducted via the open bypass valve (31a) to the feed tank by switching on the disinfecting agent unit (27) and by being conveyed by the pump (33) in order to increase the concentration of the primary circuit.

The level in the feed tank is advantageously previously reduced, for instance from 9.3 to 9.2, in order to supply a defined volume of disinfecting agent. Since the membrane (12) is impermeable to the disinfecting agent due to the reversed osmotic pressure, the ultraclean primary circuit is not contaminated by this process.

The high pressure bypass valve (13.1) is open for the duration of the disinfection in order to produce as low as possible a transmembrane pressure. Outlet valve (16) remains closed for the duration of the hot cleaning.

The flushing out process is effected by switching off the disinfecting agent supply, advantageously in two steps both for the primary side and also for the secondary side. Solution containing disinfecting agent is firstly conducted by the supply of fresh water via valve (5) to the outlet (17 or 46) until conductivity meter (22 or 23) reaches a predetermined value. After a brief standstill phase, which serves for disinfectant-containing solution to diffuse out of regions through which liquid flows poorly, a second flushing process is carried out until the predetermined conductivity boundary values are reached.

Figure 4:
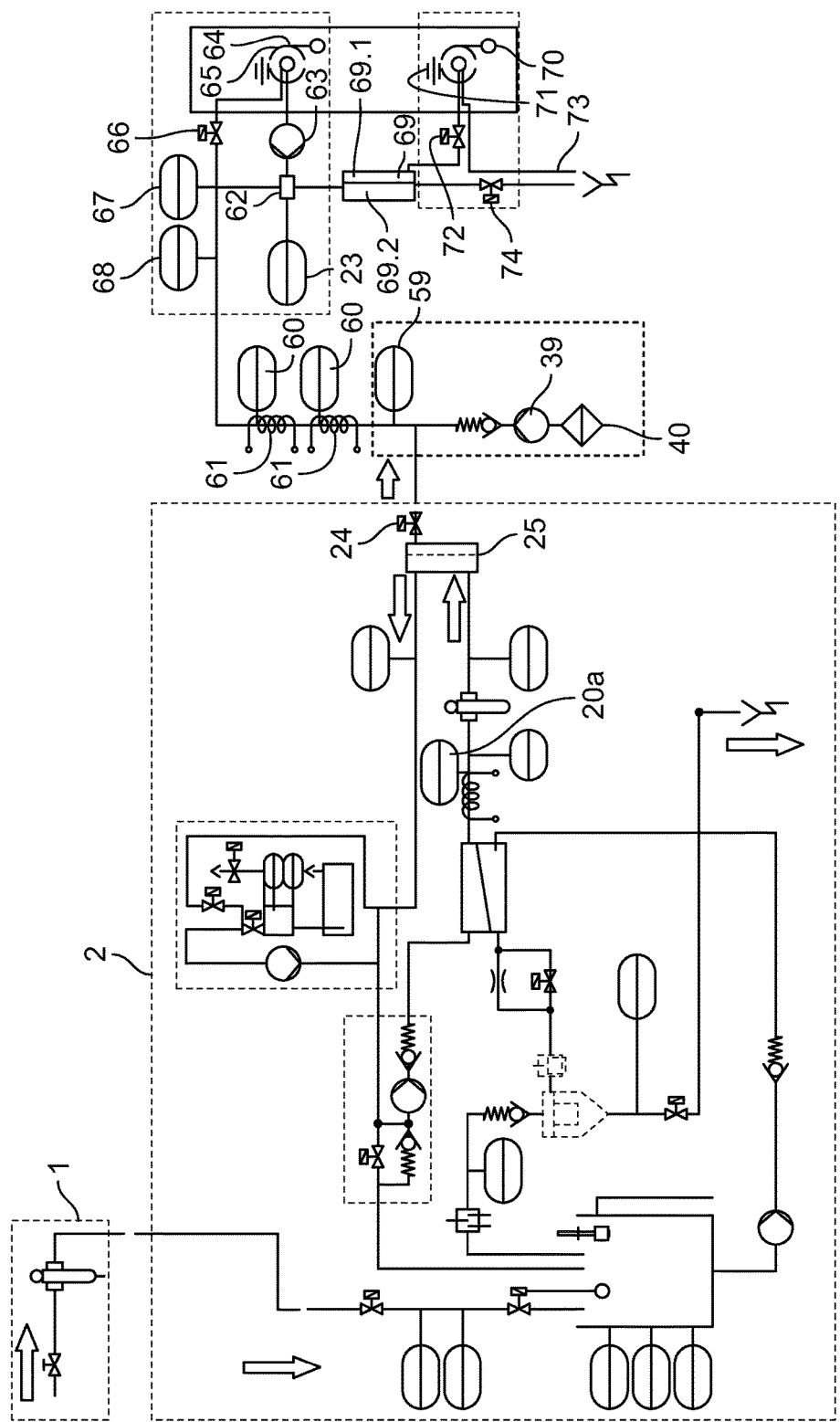
FIG. 4 is a flow plan RO with mixing installation schematic.

FIG. 4 shows in more detail the view shown schematically in FIG. 1 of a mixing installation. Released permeate flows through the permeate release valve (24) to a further heating and temperature control device (59, 60, 61, 68) and is heated to, for instance, body temperature, whereby the sensors (60, 20a) can be constructed in the form of bimetallic sensors for temperature protection. The permeate is homogenised with a concentrate, which is not shown, and is added in a metered manner by means of the concentrate pump (63) in the mixing chamber (62). The concentrate can be connected to the concentrate bag connector (65) with the valve (64) open. The finished flushing solution can be monitored by means of conductivity measuring cell (23) and flows via sterifilter (69) and flushing solution release valve (72) to the flushing solution connector (71). When the flushing solution valve (70) is open, a flushing solution tank, which is not shown, is connected by means of a suitable connecting method. The further valves (66, 74) are provided for the purpose of flushing the respective concentrate connector (64, 65) and the filter (69) and the flushing solution valve (70 and 71).

Figure 5B:
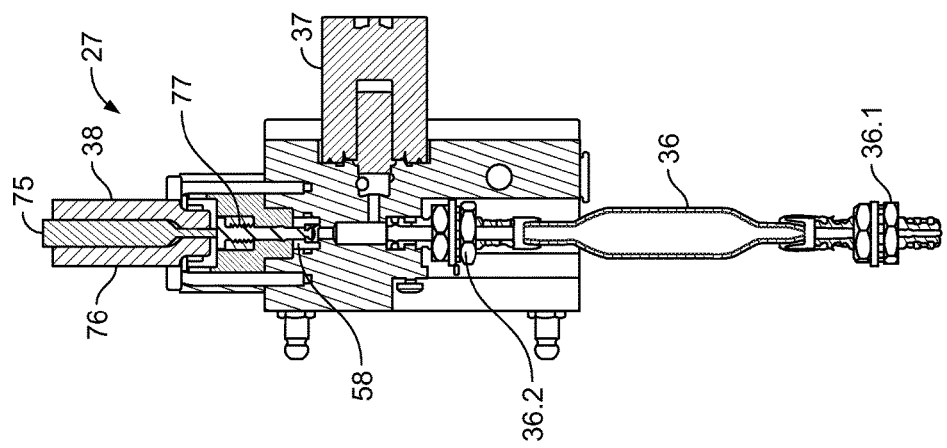
FIG. 5b is a cross-section of the disinfection block.
Figure 5A:
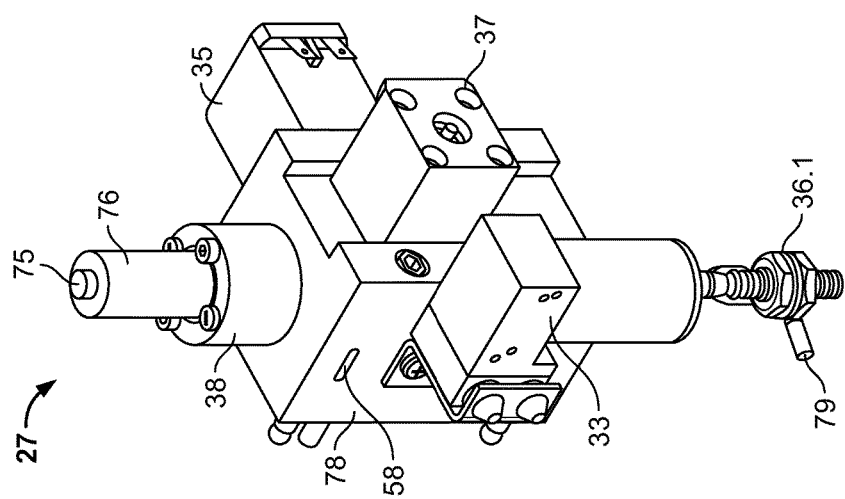
FIG. 5a is a perspective view of a disinfection block.

FIG. 5 shows the construction of the disinfecting and cleaning unit (27), the function of which was already described in FIG. 1.

The chamber with protective device (36) is shown in the form of a glass vessel (36) with its beak-shaped electrodes (36.1 and 36.2) by means of which the filling level in the vessel can be monitored. Cable connector (79) has a potential electronic connection to the electrodes 36.1 and 36.2. Valve (38) is constructed in the form of a spring-loaded magnetic lifting valve, wherein in the unpowered state the return spring (77) presses the magnetic plunger (75) upwardly and thus allows the aeration (58) of the disinfection chamber (36). A hose clamping valve is possible and usable in the place of the magnetic valve (38) illustrated here.

In order to illustrate the compact construction, the prismatic disinfecting agent block (76) has the support for the cleaning pump (33), shown here in the alternative as a membrane pump, whereby a hose pump can alternatively also be used. In order to minimise the structural size, all connections of the disinfection and cleaning unit (27) are attached on and in this block (78).

Figure 6:
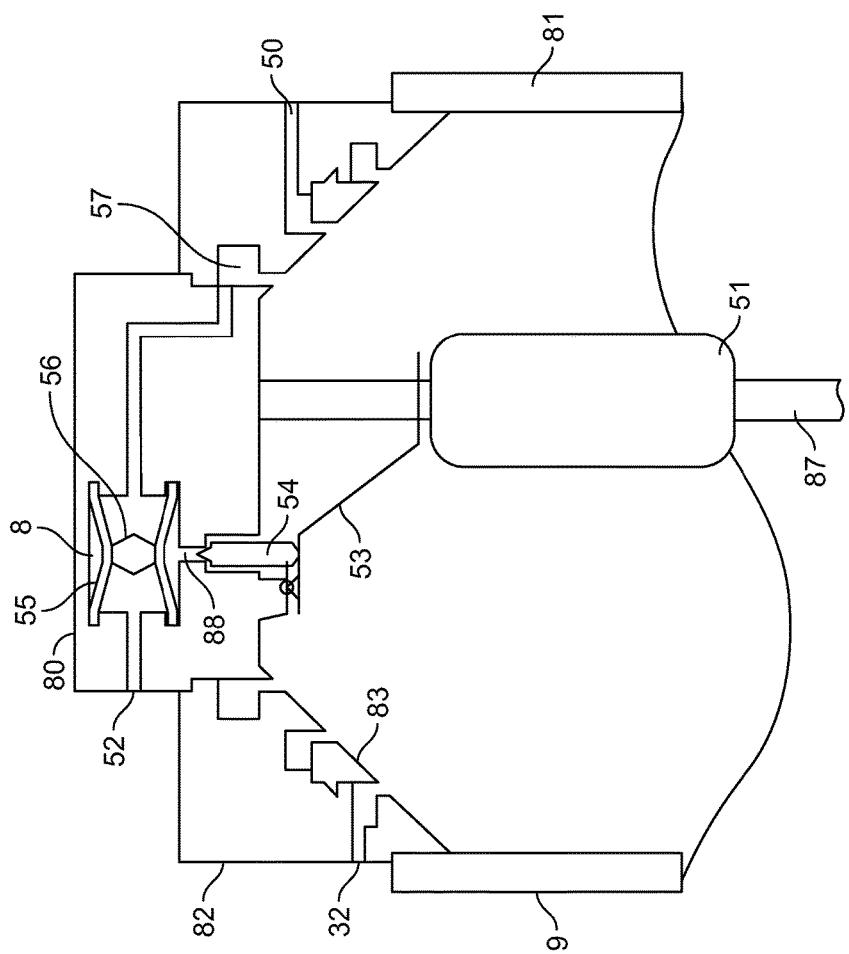
FIG. 6 is feed tank inflow schematic.

FIG. 6 is a schematic view of the continuous, calmed liquid supply into the feed tank (9).

The raw water supply (52) is moved, when the float (51) is lowered, into the annular gap (57) by the V-shaped membrane (55) pressing onto it. As a result of the geometry of the annular gap-shaped raw water inlet (57), a uniform, non-turbulent liquid supply into the feed tank is achieved. Float (51) controls the inlet of raw water by means of float lever (53), which for the purpose of force transmission has its pivot point close to the servo bore (88) and the servo bore member (54). The level sensors (9.1, 9.2, 9.3) for filling level control and indication built into the float tube (87) and the electric valve for switching off the servo flow (8.1) are not shown.

Also not shown is the overflow with detector (10) described in FIG. 1.

The feed tank is in three parts in the inlet region and consists of the feed tank head, in which the water inlet valve (8) with its servo bores is inserted, the lid with the clipped in, annular return gap (83) for permeate and concentrate feed conduit, the feed tank pipe (81) and a bottom closure member, which is not shown.

| Legends |
|---|
| 1. Prefilter |
| 2. RO installation |
| 3. Sterifilter extension |
| 4. Redundant electronic system |
| 5. Water inlet valve |
| 6. Inlet conductivity meter |
| 7. Inflow flow meter |
| 8. Float-controlled inlet valve (with electronic switch off option, 8.1) |
| 9. Feed tank with sensors for detecting empty and level control (9.1, 9.2, 9.3) |

Legends

10. Overflow with detector
11. High pressure pump
12. RO membrane, 12.1 primary side, 12.2 secondary side
13. Flow throttle with high pressure bypass valve 13.1
14. Optional centrifugal chamber/14.1 Optional cleaning chamber
15. Outlet flow meter
16. Outlet valve
17. Discharge
18. Optional temperature sensor
19. Cleaning chamber
20. Optional heater with control temperature sensor 20a
21. Temperature controller
22. Conductivity measuring cell, permeate conductivity monitor with temperature sensor
23. Redundant conductivity measuring cell and temperature indicator
24. Permeate release valve
25. Permeate Ultrafilter/Sterifilter
26. Optional flow meter
27. Disinfecting and cleaning unit
28. Permeate circulation conduit
29. Permeate circulation conduit
30. Permeate circulation pump
31. Pressure holding valve with bypass (31a)
32. Concentrate circulation conduit
33. Cleaning agent pump
34. Cleaning agent canister
35. Flushing vavle
36. Chamber with protective device against unintended disinfection with two level sensors (36.1/36.2
37. Disinfection release valve
38. Aeration valve
39. Compressed air inlet, air pump
40. Air filter
41. Metering device for concentrate/flushing solution agent
42. Optional Sterifilter
43. Outlet valves
44. Permeate feed conduit
45. Pressure sensor
46. Permeate outlet
47. Sample removal valve
48. Post-filter
49. Filtrate outlet/consumer
50. Permeate return
51. Float
52. Raw water inlet
53. Float lever
54. Servo bore closure member
55. Hose-shaped valve-shaped membrane
56. V-shaped barrier
57. Annular gap-shaped raw water inlet
58. Disinfection chamber aeration
59. Temperature sensor inlet
60. Temperature safety limiter
61. Heater No. 2
62. Mixing chamber
63. Concentrate pump
64. Concentrate valve.
65. Concentrate bag connector with monitor
66. Concentrate valve flushing valve
67. Pressure sensor
68. Temperature controller
69. Sterifilters 69.1 Filtrate side 69.2 Primary side
70. Flushing solution valve
71. Flushing solution connector with monitor
72. Flushing solution release valve
73. Flushing solution outlet
74. Flushing solution bypass valve
75. Magnetic plunger
76. Coil
77. Return spring
78. Disinfection block
79. Cable connector
80. Feed tank head
81. Feed tank pipe
82. Feed tank cover
83. Feed tank permeate return annular gap
84. High pressure conduit

Legends

85. Flushing connector
86. Disinfecting agent supply
87. Float tube
88. Servobore
89.

The invention claimed is:

1. An RO installation for verifying a reverse osmosis (RO) membrane, the RO membrane being in the RO installation, characterised in that conductivity values of supplied raw water and of a permeate and an amount of raw water inflow and of concentrate outflow are measured continuously or cyclically and that efficiency of the RO membrane and its retention rate and/or filtration efficiency are calculated from the measured conductivity values and amount of raw water inflow and concentrate outflow, wherein the conductivity values of the supplied raw water are measured directly from a raw water supply, wherein the efficiency of the RO membrane is calculated from a ratio of an amount of the permeate to the measured amount of the raw water inflow, the amount of the permeate being calculated from the measured amount of raw water inflow and the measured amount of the concentrate outflow, wherein the retention rate of the RO membrane is calculated from a ratio of the measured conductivity value of the permeate to the directly measured conductivity value of the supplied raw water, and wherein the filtration efficiency of the RO membrane is assessed using the retention rate, the RO installation comprising:

a raw water supply conduit (1a) providing the raw water supply, which raw water supply conduit leads to a feed tank (9), from which a conduit (84) with a pump (11) leads to the primary side (12.1) of an RO membrane (12), from where a concentrate circulation conduit (32) leads back to the feed tank (9), and a permeate feed conduit (44) and a first permeate circulation conduit (28), which either extends to a permeate return conduit (50), which leads to the feed tank (9), or communicates via a further permeate circulation conduit (29) with the secondary side (12.2) of the RO membrane, and a filtrate outlet conduit including an ultrafilter (25) having a membrane with a secondary side which leads to another ultrafilter (42) having a membrane with a secondary side that leads to a filtrate discharge (49), characterised in that arranged in the raw water supply conduit (1a) there is a supply flow meter (7) and in a concentrate outlet conduit (32a) there is an outflow flow meter (15), which are monitored by associated, independent computers and whose measurement values are analysed to determine the efficiency of the RO membrane (12), characterised in that arranged in the raw water supply conduit (1a) there is an inlet conductivity measuring cell (6) and in the permeate feed conduit (44) there is a permeate conductivity measuring cell (22) connected to at least one computer, wherein values from the permeate conductivity measuring cell are measured by the at least one computer and are analyzed to determine the retention rate of the RO membrane (9).

2. An RO installation as claimed in claim 1, characterised in that the raw water supply conduit (1a) communicates with an annular gap (57) in the feed tank (9), through which there is a uniform, non-turbulent water supply into the feed tank, which enables an exact, volumetric measurement of the inflow and outflow.

3. An RO installation as claimed in claim 1, characterised in that the permeate feed conduit (44) leads to an ultrafilter/sterifilter (25), leading off from whose primary side is the first permeate circulation conduit (28) and going off from whose secondary side is the filtrate outlet conduit and that inserted at a filtrate outlet of the ultrafilter/sterifilter (25) there is a blocking valve (24) which stops a filtrate outflow in the event of defective process data.

* * * * *